United States Patent [19]

Bottum

[11] E Re. 29,737

[45] Reissued Aug. 22, 1978

[54] SOLAR COLLECTOR

[76] Inventor: Edward W. Bottum, 9357 Spencer Rd., Brighton, Mich. 48116

[21] Appl. No.: 820,583

[22] Filed: Aug. 1, 1977

Related U.S. Patent Documents

Reissue of:

[64] Patent No.: 4,026,277
Issued: May 31, 1977
Appl. No.: 586,612
Filed: Jun. 13, 1975

[51] Int. Cl.[2] ..... F24J 3/02

[52] U.S. Cl. ..... 126/271; 29/157.3 C; 228/248

[58] Field of Search ..... 237/1 A; 126/270, 271; 228/248; 29/157.3

[56] References Cited

U.S. PATENT DOCUMENTS

| | | | |
|---|---|---|---|
| 1,338,644 | 4/1920 | Arthur et al. | 126/271 |
| 2,316,191 | 4/1943 | Scott | 126/271 |
| 2,917,817 | 12/1959 | Tabor | 126/270 X |
| 3,432,910 | 3/1969 | Bottum et al. | 228/248 X |
| 3,750,747 | 8/1973 | Hingorany | 228/248 X |
| 3,916,871 | 11/1975 | Estes et al. | 126/271 |

FOREIGN PATENT DOCUMENTS

| | | | |
|---|---|---|---|
| 869,747 | 6/1961 | United Kingdom | 126/271 |

*Primary Examiner*—Kenneth W. Sprague
*Attorney, Agent, or Firm*—Whittemore, Hulbert & Belknap

[57] ABSTRACT

A solar collector of the type used to convert the sun's light rays into heat energy is provided. The solar collector includes a steel plate to absorb the sun's rays. A flat coil of tubular steel is attached to the steel plate by means of the hydrogen brazing process. The surfaces of the steel plate and the tubular coil are preferably coated with a thin layer of copper to form a selective surface to promote the efficient collection of energy.

5 Claims, 5 Drawing Figures

FIG. 1
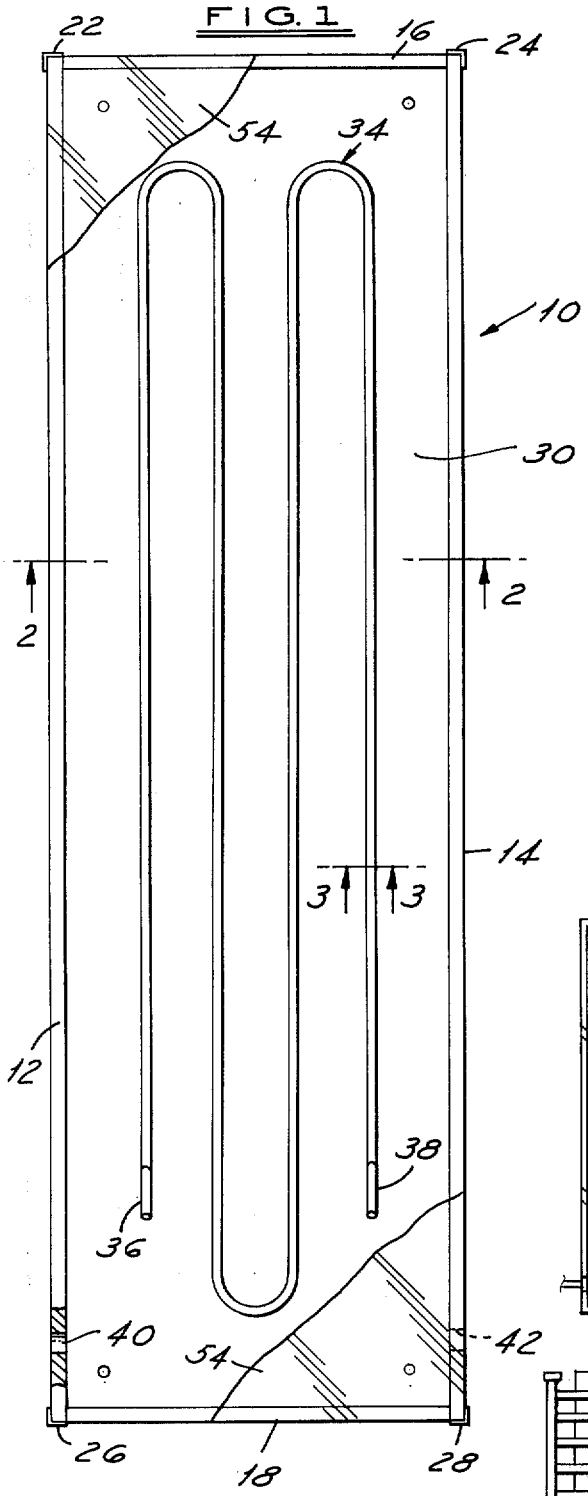
FIG. 2
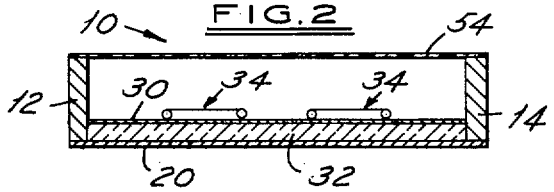
FIG. 3
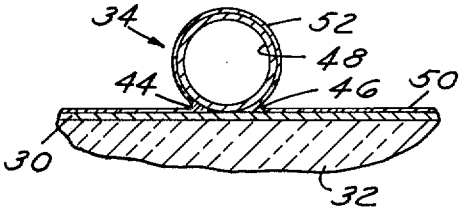
FIG. 4
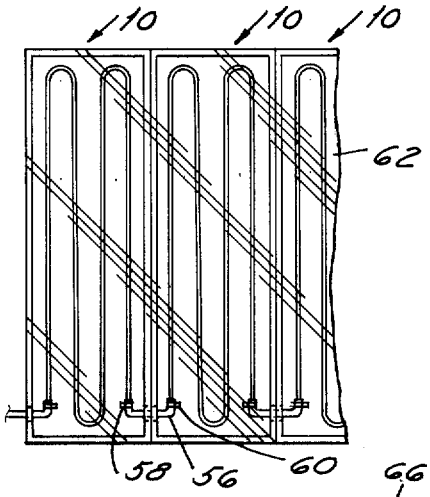
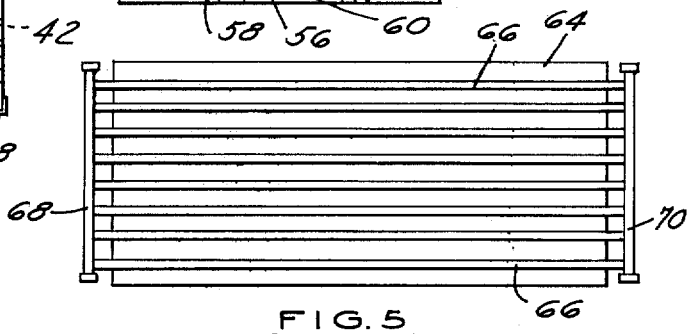
FIG. 5

SOLAR COLLECTOR

Matter enclosed in heavy brackets [ ] appears in the original patent but forms no part of this reissue specification; matter printed in italics indicates the additions made by reissue.

BACKGROUND OF THE INVENTION

Solar collectors are used to convert the sun's rays into heat energy, usually transferring this heat to a liquid or gas which may be transported to a point of use.

One type of conventional collector includes a flat plate to which is attached a metallic tubular coil. The flat plate is adapted to collect the sun's rays, convert these rays to heat energy and conduct this heat energy to the tubular coil. A fluid, either a gas or liquid, is circulated through the coil. The fluid is heated in the process. The heated fluid is then transported to some other location where heat energy is extracted normally for the ultimate purpose of heating a building structure or water, or cooling a building by means of absorption refrigeration.

In one form of collector, the flat plate has been fabricated of aluminum. Aluminum has the drawback of being subject to electrolysis with resultant corrosion. Unless careful precautions are taken, aluminum structure may deteriorate rapidly.

In another form, the flat plate and tubular coil are fabricated of copper which has been considered the best material for solar collectors. Copper provides almost twice the conductivity of aluminum. However, the cost of copper is extremely high. The total area required in many cases may result in the cost of the solar collector being prohibitive.

Copper collectors usually consist of a hairpin or serpentine (or other) flat copper tubing attached to a copper plate. The coil may be mechanically held against the plate by means of a clamp. More often, the coil is soft soldered to the plate by means of a lead-tin solder. In either case, the method of attaching the coil to the plate is considered to be a bottleneck in the transfer of heat from the plate to the coil. A mechanical joint does not provide the best heat transfer connection. Additionally, corrosion, which generally occurs after a period of use, results in the mechanical joint being even less effective. The "soft solder" connection also often used is a bottleneck because the conductivity of lead-tin solder is only one-eighth that of copper and "soft solder" is also susceptible to corrosion.

Steel has not been extensively used in the past for solar collector flat plates or tubular coils because of the generally low heat conductivity properties of steel. In accordance with the present invention, a flat steel plate and steel tubular coil are used. The steel coil is hydrogen copper brazed to the flat steel plate. This process results in a fillet on each side of the tube and a flat pool of copper between the fillets joining the steel tube and steel plate. The result is that heat is conducted from the steel plate to the steel tube at approximately ten times the rate that it would be in an all copper collector where the conduction between plate and tube is made through lead-tin solder or a mechanical connection. While it is true that copper is a much better conductor than steel, the relatively low cost of steel permits heavier gages of steel to be used thereby offsetting some of this advantage. The steel tubes may also be placed closer together thereby further reducing the advantage of the superior heat conductivity enjoyed by copper. By this means, the performance difference between a collector employing copper and a collector employing steel as the collecting device is practically eliminated.

A further advantage of the present invention is that hydrogen copper brazing is a more economical way to attach a coil to a plate than is soft soldering. Copper plates and tubing could not be hydrogen copper brazed because in this process, the structure is passed through a hydrogen atmosphere control furnace at approximately 2100° Fahrenheit. At this temperature, copper melts which in the nature of things is desired in connection with brazing steel parts together but would be impossible for use in connection with brazing copper parts together. Hydrogen brazing is also desirable because it is a clean process minimizing the necessity to clean the finished parts.

In essence, the hydrogen copper brazed steel collector can approach the efficiency of a copper collector and possibly in some cases exceed such efficiency. However, the hydrogen copper brazed steel collector is only a fraction of the cost of a copper tubing and copper plate collector.

SUMMARY OF THE INVENTION

The solar collector comprises a housing in which a steel plate is mounted to absorb sun rays and convert such rays to heat energy. Steel tubing is secured to the plate for conduction of heat energy from the plate to the tubing. The tubing is adapted for the flow of fluid therethrough to transfer heat energy from the solar collector to a point of use. A copper bond is brazed between the tubing and the plate, forming both a mechanical bond and a heat conducting medium. A transparent plate is provided on the housing to permit sun rays to impinge upon the steel plate.

IN THE DRAWING:

FIG. 1 is a top plan view of one embodiment of the solar collector of the present invention;

FIG. 2 is a sectional view taken substantially along the line 2—2 of FIG. 1 looking in the direction of the arrows;

FIG. 3 is a sectional view taken substantially along the line 3—3 of FIG. 1 looking in the direction of the arrows; and FIG. 4 is a top plan view illustrating connection of three of the solar collectors of FIG. 1 together to form a unitary solar collector of greater capacity than a single collector unit.

FIG. 5 illustrates another embodiment.

The solar collector 10 includes an elongated housing comprising side walls 12, 14, end walls 16, 18 and bottom wall 20. These housing elements are preferably fabricated of treated wood which resists deterioration when exposed to the weather. The housing is secured together by means of metallic end corners 22, 24, 26, 28. Screws may be used as fastening devices.

A flat steel plate 30 is provided within the housing spaced from the bottom wall 20. Heat insulating material 32 is provided in the space between the bottom wall 20 and plate 30. This heat insulation prevents loss of heat from the plate 30 through the bottom of the housing. A steel tubular coil 34 is attached to the plate 30 by means of hydrogen-copper brazing. The runs of the coil 34 are closely spaced together to maximize heat transfer between the plate 30 and the coil. The ends 36, 38 of the coil are bent upwardly slightly to permit connection to a hose for the circulation of fluid, either a liquid or a gas, through the coil. Openings 40, 42 are provided in side walls 12, 14 for insertion of hoses into the housing for connection to the coil 34.

Referring to FIG. 3, it will be noted that the coper fillets 44, 46 are brazed on either side of tube section 48 forming part of the coil 34. These fillets extend for the entire length of the coil. The fillets provide a mechanical connection between the coil and the plate. Additionally, the fillets provide a heat conductor between the plate 30 and coil 34. It will be noted that the fillets are relatively thick, not only providing the structure necessary to bond the coil to plate 30 but also additional material to improve heat conductivity between the plate and coil. What is termed a "selective surface" 50 is also provided on the surface of plate 30 when the coil 34 is hydrogen brazed thereto. A selective surface is a surface provided on a collector plate to improve the energy collecting ability of the plate. In the present instance, this selective surface is also provided over the coil so that the coil itself may directly absorb sun energy.

A method for both hydrogen-copper brazing the coil 34 to the plate 30 and also providing selective surface 50 on the plate 30 and an additional selective surface 52 on the coil 34 is disclosed in U.S. Pat. No. 3,432,910. In this method, a copper-containing brazing material is first provided at the joint of the coil and plate as a relatively thick layer. The entire exterior surface of both the plate and coil is then coated with a copper-containing material in finely divided form in a liquid carrier. The assembly is then dried to form a thin layer of the brazing material in finely divided form over the entire surface. The assembly is then subjected to heat in a brazing furnace preferably having [an inert] *a reducing* atmosphere. The heating is continued for a time sufficient to braze the joint and braze the relatively thin layer to form a continuous coating over the entire exterior surface of the assembly. The surface of the assembly is preferably first prepared by roughening or by uniformly oxidizing before application of the thin layer of brazing material. This step improves the adhesion of the layer.

The copperized surface thus provided over the plate and coil results in several advantages. First, this surface provides an improved selective surface to prevent reflection and to trap the sun's rays causing them to be converted to heat energy on the collector plate surface. Secondly, the copperized surface improves the heat conductivity of the plate. Finally, the copperized surface protects the steel coil and plate from corrosion.

Other selective surfaces may be used. Such other selective surfaces may be applied by a plating process or may be painted on. For example, a coat of paint may first be applied to protect the steel against corrosion, a second coat may be provided to improve the heat conductivity and a final coat may be provided to prevent reflection and trap the sun's rays, causing them to convert to heat energy on the collector surface.

A transparent cover plate 54 is secured to the top of the housing. The plate 54 may be, for example, clear glass or plastic. Preferably, either the glass or plastic is treated so as to tend to pass light rays into the collector while resisting passage of reflected rays back through in the opposite direction. For example, sheet glazing material such as PVF film type 400BG200TR, sold by the DuPont Company under the trademark "Tedlar" may be adhered to the outer surface of plate 54.

A single layer of "Tedlar" film is satisfactory for applications where liquid is to leave the collector at low temperatures, such as for use with a solar assisted heat pump. However, where higher liquid temperatures are required, double glazing is usually necessary. Preferably the two layers of "Tedlar" should be separated by a minimum of one-half inch, although little would be gained by separating the layers by over three-fourth inch.

Individual collectors 10 are readily joined together in series as shown in FIG. 4 by means of hoses 56, and clamps 58, 60 to form a battery of collectors. If a large number of collectors 10 are to be connected together in a bank, it is preferable that they be connected in parallel to reduce the pressure drop.

FIG. 5 illustrates another embodiment which employs a different type of coil arrangement. The collector plate 64 is the same as previously described and is adapted to be mounted in a housing as described.

Instead of a serpentine coil as in FIG. 1, the coil comprises a plurality of spaced apart tubes 66 which are connected at each end to a pair of manifolds 68, 70. Fluid is pumped into one of the manifolds, passes through the tubes 66 and is extracted via the other manifold.

The tubes 66 are brazed to plate 64 as previously described and the surface of plate 64 and tubes 66 may be copperized in the manner previously described.

What I claim as my invention is:

1. A solar collector comprising a housing, a steel plate within the housing to absorb sun rays and convert such rays to heat energy, steel tubing secured to the plate for conduction of heat energy from the plate to the tubing, said tubing being adapted for the flow of fluid therethrough to transfer heat energy from the solar collector to a point of use, a copper bond brazed in [an inert] *a reducing* atmosphere between said tubing and the plate forming both a mechanical bond and a heat conducting medium, and transparent plate means on the housing to permit sun rays to impinge upon the steel plate.

2. A solar collector as defined in claim 1, further characterized in that said copper bond comprises a relatively thick fillet.

3. A solar collector as defined in claim 2, further characterized in that a fillet is provided on each side of the tubing, said fillets extending the length of the tubing.

4. A solar collector as defined in claim 1, further characterized in the provision of a relatively thin layer of copper brazed in [an inert] *a reducing* atmosphere onto said steel plate.

5. A solar collector as defined in claim 4, further characterized in that said layer of copper also extends over the surface of said tubing.

* * * * *